(12) United States Patent
Lindenthaler

(10) Patent No.: US 7,069,082 B2
(45) Date of Patent: Jun. 27, 2006

(54) PACEMAKER FOR BILATERAL VOCAL CORD AUTOPARALYSIS

(75) Inventor: Werner Lindenthaler, Oberperfuss (AT)

(73) Assignee: MED-EL Elektromedizinische Gerate GmbH, Innsbruck (AT)

( * ) Notice: Subject to any disclaimer, the term of this patent is extended or adjusted under 35 U.S.C. 154(b) by 62 days.

(21) Appl. No.: 10/117,437

(22) Filed: Apr. 5, 2002

(65) Prior Publication Data

US 2002/0156507 A1 Oct. 24, 2002

Related U.S. Application Data

(60) Provisional application No. 60/281,746, filed on Apr. 5, 2001.

(51) Int. Cl.
*A61N 1/18* (2006.01)

(52) U.S. Cl. .................................................. 607/41

(58) Field of Classification Search ............. 607/47, 607/72, 41
See application file for complete search history.

(56) References Cited

U.S. PATENT DOCUMENTS

| 4,341,221 A | 7/1982 | Testerman .................. 128/642 |
| 4,907,602 A | 3/1990 | Sanders ....................... 128/787 |
| 5,016,647 A * | 5/1991 | Sanders ........................ 607/72 |
| 5,111,814 A | 5/1992 | Goldfarb ................ 128/419 R |
| 5,350,413 A | 9/1994 | Miller .......................... 607/61 |
| 5,387,259 A | 2/1995 | Davidson ..................... 128/630 |
| 5,897,579 A | 4/1999 | Sanders ........................ 607/42 |
| 6,361,494 B1 | 3/2002 | Lindenthaler ............... 600/373 |

OTHER PUBLICATIONS

International Search Report for International Application No. PCT/IB 02/02274 with International Filing Date Apr. 5, 2002 and mailed Jan. 20, 2003.

* cited by examiner

*Primary Examiner*—Jeffrey R. Jastrzab
(74) *Attorney, Agent, or Firm*—Bromberg & Sunstein LLP

(57) ABSTRACT

A pacemaker system for a human subject having bilateral vocal cord paralysis includes a sensing electrode for detecting inspiratory activity of a vocalizing muscle of the subject and generating a first signal, and a processor for receiving the first signal from the sensing electrode and generating a second signal. The second signal is substantially synchronous with the first signal. A stimulating electrode receives the second signal from the pulse generator and stimulating a vocalizing nerve of the subject.

62 Claims, 6 Drawing Sheets

PACEMAKER FOR BILATERAL VOCAL CORD AUTOPARALYSIS

This application claims priority from provisional U.S. patent application Ser. No. 60/281,746 filed Apr. 5, 2001, the disclosure of which is incorporated herein, in its entirety, by reference.

TECHNICAL FIELD

The present invention relates to the treatment vocal cord autoparalysis, and in particular, to devices and methods for stimulating the recurrent laryngeal nerve of a human subject.

BACKGROUND TO THE INVENTION

Bilateral trauma to the recurrent laryngeal nerve ("RLN") causes severe dyspnea because of the paramedian position assumed by paralyzed vocal cords and the resultant loss of inspiratory abduction. Although regeneration of nerve fibers innervating the laryngeal muscles occurs in a large proportion of damages, the reinnervated vocal cord is not capable of abduction and, therefore, continues to act as an obstruction in the airway.

One reason that the reinnervated vocal cord is not capable of abduction is that the innervation is misdirected (a condition known as synkinetic innveration). Synkinetic innervation occurs when abductor fibers reach and reinnervate the adductor muscles and vice versa. Consequently, contraction of the adductor muscles occurs during inspiration, so that any inspiratory contraction of the re-innervated posticus muscle is nullified as an abductor force (a condition known as autoparalysis). Since the inspiratory fibers are randomly grouped within the trunk of the RLN, there is no known way of preventing misdirected regeneration of nerve fibers.

Alternatively, the reinnervated vocal cord may not be capable of abduction because of a reduction in the number of re-innervated motor units, (sometimes associated with trophic changes of muscle fibers), disturbance of nerve conductivity, or less maturation of neuromuscular junctions.

SUMMARY OF THE INVENTION

In accordance with a first embodiment of the invention, a pacemaker system for a human subject having bilateral vocal cord paralysis includes a sensing electrode for detecting inspiratory activity of a vocalizing muscle of the subject and generating a first signal, and a processor for receiving the first signal from the sensing electrode and generating a second signal. The second signal is substantially synchronous with the first signal. The system also includes a stimulating electrode for receiving the second signal from the pulse generator and stimulating a vocalizing nerve of the subject. In accordance with related embodiments, the system may be partially or totally implantable.

In accordance with additional related embodiments, the system may further include an energy coupling circuit that inductively couples energy for the system through the skin of the subject. Similarly, the system may include an energy coupling circuit that optically couples energy for the system through the skin of the subject. The vocalizing muscle may include an infrahyoidal muscle and/or the diaphram of the subject. The vocalizing nerve may include the recurrent larynegeal nerve of the subject or the vagus nerve of the subject.

In accordance with a further related embodiment, the processor may detect when the first signal has reached a predetermined level and respond by generating the second signal. Additionally, the processor include a pulse generator. In accordance with other related embodiments, the electrodes may be bipolar or tripolar. The second signal may be a biphase current pulse, and current pulse may have a duration of about 0.1 msec to 2 msec and a magnitude in the range of about 0.5 mA to 5.0 mA.

In accordance with another embodiment of the invention, pacemaker for a human subject having bilateral vocal cord autoparalysis includes a sensing electrode for detecting inspiratory activity of a vocalizing muscle of the subject and generating a first signal. The pacemaker also includes a processor for receiving the first signal from the sensing electrode and generating a second signal, the second signal being substantially synchronous with the first signal, and a stimulating electrode for receiving the second signal from the processor and stimulating a vocalizing nerve of the subject to open the vocal cord and permit inspiration.

In accordance with a further embodiment of the invention, a method for stimulating a vocalizing nerve in a in a human subject having bilateral vocal cord autoparalysis includes detecting inspiratory activity of a vocalizing muscle of the subject with a first electrode and generating a first signal. The first signal is transmitted to a processor, and the processor generates a second signal. The second signal is substantially synchronous with the first signal, and is received at a second electrode. The second electrode then stimulates a vocalizing nerve of the subject in accordance with the second signal. In accordance with a related embodiment of the invention, the method further includes providing an energy coupling circuit that inductively couples energy through the skin of the subject. In accordance with another related embodiment, the method includes providing an energy coupling circuit that optically couples energy through the skin of the subject.

In accordance with another embodiment of the invention, a method for pacing laryngeal activity of a human subject includes sensing electrical activity of a vocalizing muscle of the subject and artificially stimulating a vocalizing nerve of the subject with an electrical signal in synchronism with the sensed electrical activity. In accordance with a related embodiment, artificially stimulating the vocalizing nerve of the subject with an electrical signal includes stimulating the nerve with an electrical signal at a frequency that is approximately reciprocal to the contraction time of the vocal cord abductor of the subject. In accordance with another related embodiment of the invention, artificially stimulating the vocalizing nerve of the subject with an electrical signal includes stimulating the nerve with an electrical signal at a frequency that is below the reciprocal of the contraction time of the vocal cord adductor of the subject.

In accordance with yet another embodiment of the invention, a method for pacing laryngeal activity of a human subject includes sensing electrical activity of a vocalizing muscle of the subject and artificially stimulating a vocalizing nerve of the subject in synchronism with the sensed electrical activity during inspiration such that the vocal folds passively relax backwards to the midline.

BRIEF DESCRIPTION OF THE FIGURES

The foregoing features of the invention will be more readily understood by reference to the following detailed description taken with the accompanying drawings in which.

DETAILED DESCRIPTION OF SPECIFIC EMBODIMENTS

Figure 1:
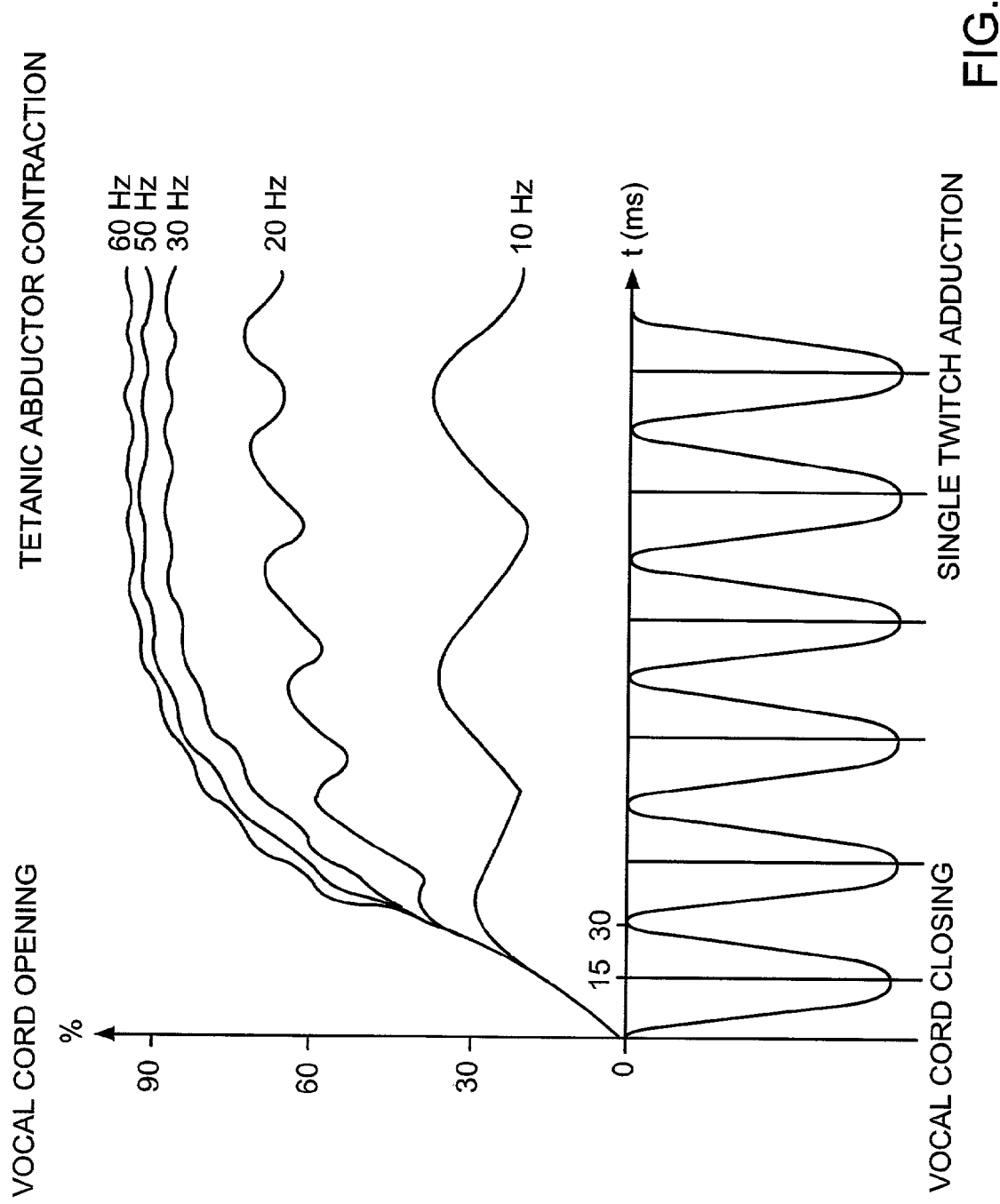
FIG. 1 is a graphical illustration of the underlying principle of frequency-dependent movement of the vocal cords in accordance with an embodiment of the present invention.

The underlying principle for stimulation with the device and methods of the invention is the frequency-dependent movement of the vocal cords due to RLN stimulation, as shown in FIG. 1. Such movement occurs as a result of the difference in contraction times between the abductor and adductor muscles. The contraction time of the only existing abductor of the vocal cords, the posterior cricoarytenoid ("PCA") muscle, is significantly longer than that of the adductor muscles. The RLN contains the nerve fibers to all muscles that act on the vocal cords (except the cricothyroid ("CT") muscle which is innervated by the superior laryngeal nerve ("SLN")), randomly distributed over the whole nerve. Consequently, an action potential generated by an electrical stimulation always reaches both abductor and adductor muscles. Thus, the glottis first closes due to the faster adductors, then it opens, and ends with relaxation which leads to a vibration of the vocal cords.

When stimulated at a frequency approximately reciprocal to the contraction time of the vocal cord abductor, the action potentials arrive at the muscles at a time when the adductor muscles will have just relaxed from the last activation when the next pulse arrives (as shown below the zero-line on the graph). The abductor, in contrast, has just reached its maximal contraction when the incoming initiation for the next contraction causes their temporal summation (shown above the zero-line). Consequently, resulting tetanic abductor tension overcomes the weaker single twitch adduction.

For stimulation at a frequency approximately reciprocal to the contraction time of the vocal cord adductor the adductor muscles also reach tetanic contraction, and due to their greater number (4:1) the vocal cords are closed. This frequency selective principle is still intact after misdirected (synkinetic) re-innervation in a slightly reduced manner, because it depends on a property of the muscles, and not of the nerve. When the whole RLN is stimulated, the misdirected fibers carry the rate of the action potentials to muscles, and these are activated selectively according their own contraction time. This is possible, because the PCA muscle fibers indicate a high degree of resistance to alteration of their normally oxidative profile and of the acid stability of their myosin ATPase enzymes even when re-innervated by fast motor nerves.

The synkinetically re-innervated nerve, and not the muscle directly, is stimulated, because more than a decade less power is necessary for activation of a nerve than of the muscle itself. Additionally, the nerve-cuff-electrode can be positioned along the nerve far from moving muscles and tissue and far from sensitive receptors, which would produce unwanted reactions.

Figure 2:
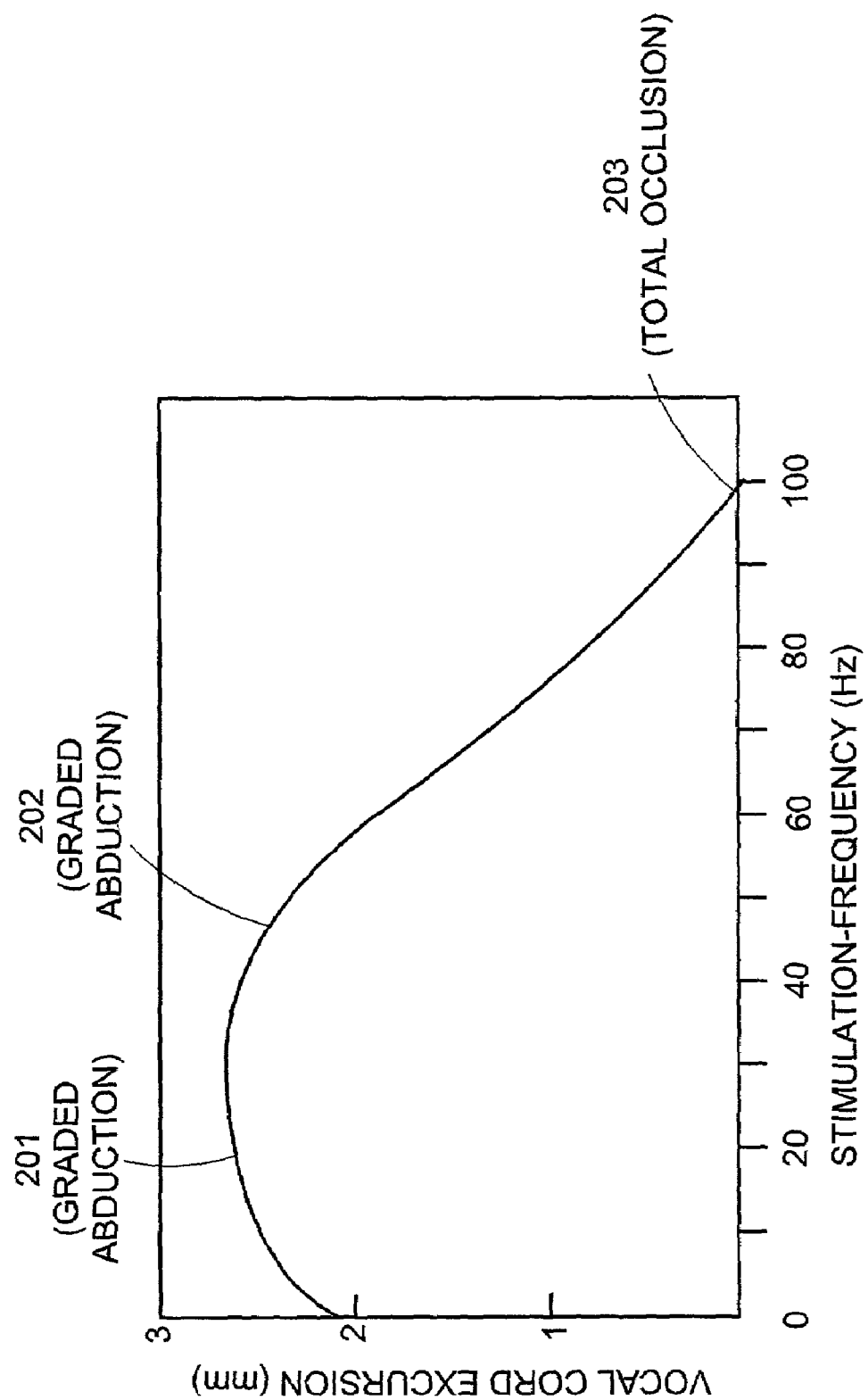
FIG. 2 is a graphical illustration of the frequency-dependent motion of the vocal cords in accordance with the embodiment of FIG. 1.

FIG. 2 is a graphical illustration of the frequency-dependent motion of the vocal cords. Stimulation at 10 to 30 Hz causes a graded abduction 201 of the vocal cords. Above 30 Hz graded cord adduction occurs 202, with total airway occlusion 203 at 100 Hz by bilateral stimulation.

Figure 3A:
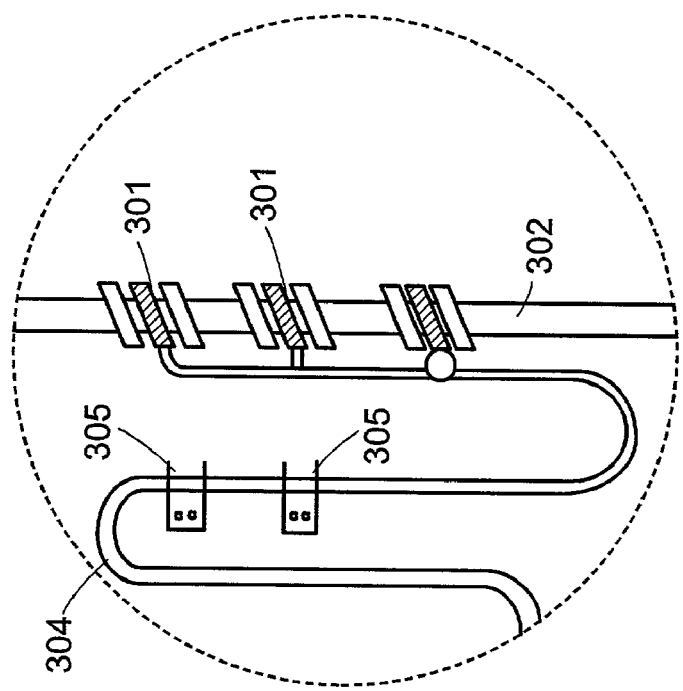
FIG. 3 is an illustration of the complete stimulation system in accordance with another embodiment of the invention.
Figure 3:
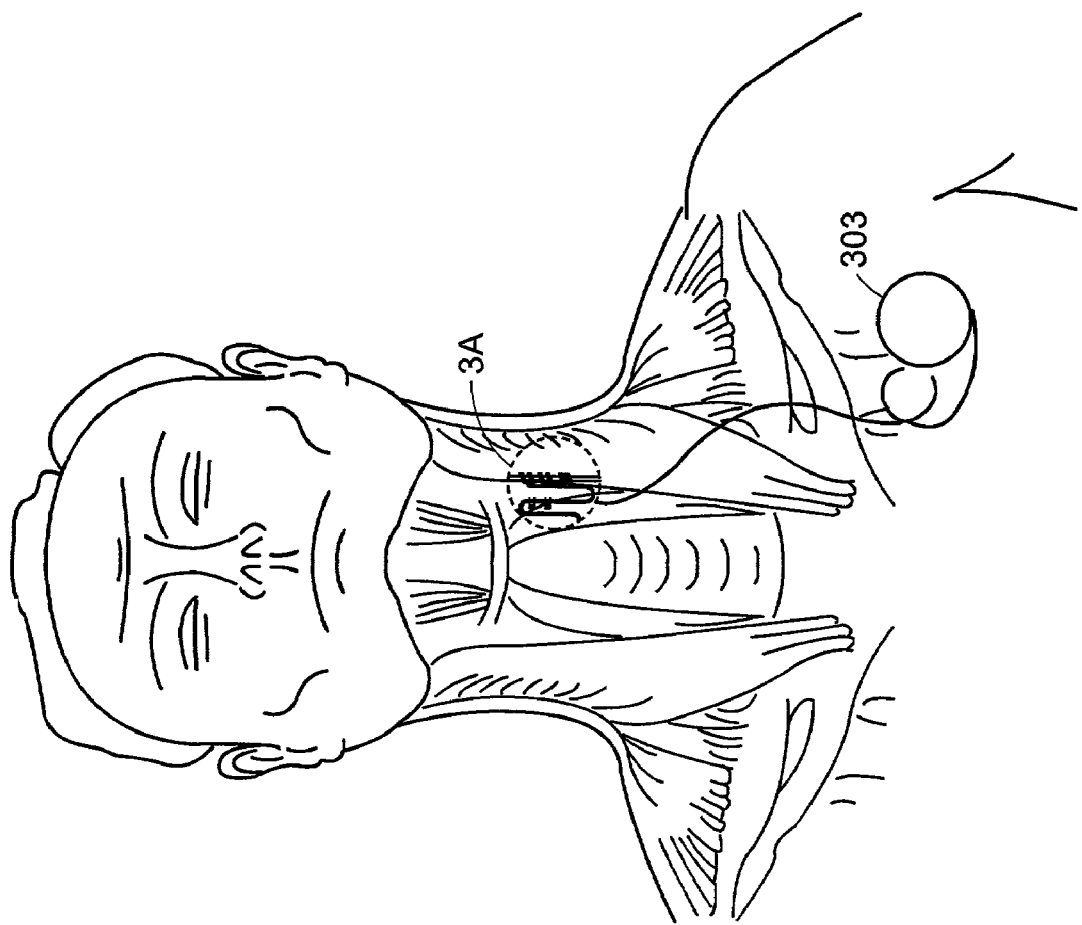

FIG. 3 is an illustration of the complete stimulation system. The pacemaker system for bilateral vocal cord autoparalysis is comprised of one or more stimulating (efferent) electrodes 301, one or more sensing (afferent) electrode (not visible) and a processor 303, which in this embodiment includes a pulse generator. In accordance with FIG. 3, the processor 303 is implanted in the patients chest, and the helical stimulating electrodes 301 are wrapped around the vagus or recurrent laryngeal nerve 302 along with the electrode leads 304 and safety loops 305.

The system may be totally or partially implanted in a human subject. The stimulator may include a housing that can be very small with all of the implant's electronic components contained in a robust and compact hermetically sealed case. Energy and necessary information may be inductively or optically transferred through the skin of the subject. This can be achieved by either enclosing the electronic circuitry inside a metallic case with a secondary coil placed aside or around the case. Similarly, this may be achieved by enclosing the electric circuitry and a secondary coil inside a dielectric case.

The sensing (afferent) part of the closed loop system consists of an electrode, that detects the inspiratory activities of the infrahyoidal muscles or the diaphragm of a human subject, (that is, their innervating nerves, depending on which measurement, or what combination of measurements, delivers the most inspiration-synchronous signal). In accordance with an embodiment of the invention, such stimulation is limited to the inspiratory phase of respiration. During non-inspiratory phases, the vocal folds passively relax backwords to the midline, allowing for normal voice production and airway protection. The sensing electrode generates a first signal in response to activity that has been detected. The processor 303 receives the first signal from the sensing electrode and generates a second signal. The second signal is substantially synchronous with the first signal. Further, the second signal may be a biphase current pulse, and the biphase current pulse may have a duration of about 0.1 msec to 2 msec and a magnitude in the range of about 0.5 mA to 5.0 mA.

A stimulating electrode 301 receives the second signal from the pulse generator and stimulates the recurrent larynegeal nerve, or alternatively the vagus nerve (from which the RLN originates and which is easier to handle surgically). The stimulating electrodes and the sensing electrodes may be either bipolar or tripolar. Similarly, one electrode may be bipolar and one electrode may be tripolar. The electrode leads 304 should be sufficiently damage-resistant. The lead body should be arranged in a way, so that the nerve and the stimulator are influenced as little as possible by movements of the muscles, the neck and the head.

The above mentioned principle can also be used to activate the vocal cord abduction autoparalysis patients (where the PCA is re-innervated but in a misdirected way) by stimulating the whole innervating recurrent laryngeal nerve or alternatively, the vagus nerve, from which the RLN originates. The principle is effective with respect to the treatment of autoparalysis patients because it is based on a muscle characteristics and not on nerve or muscle/nerve characteristics.

Figure 4:
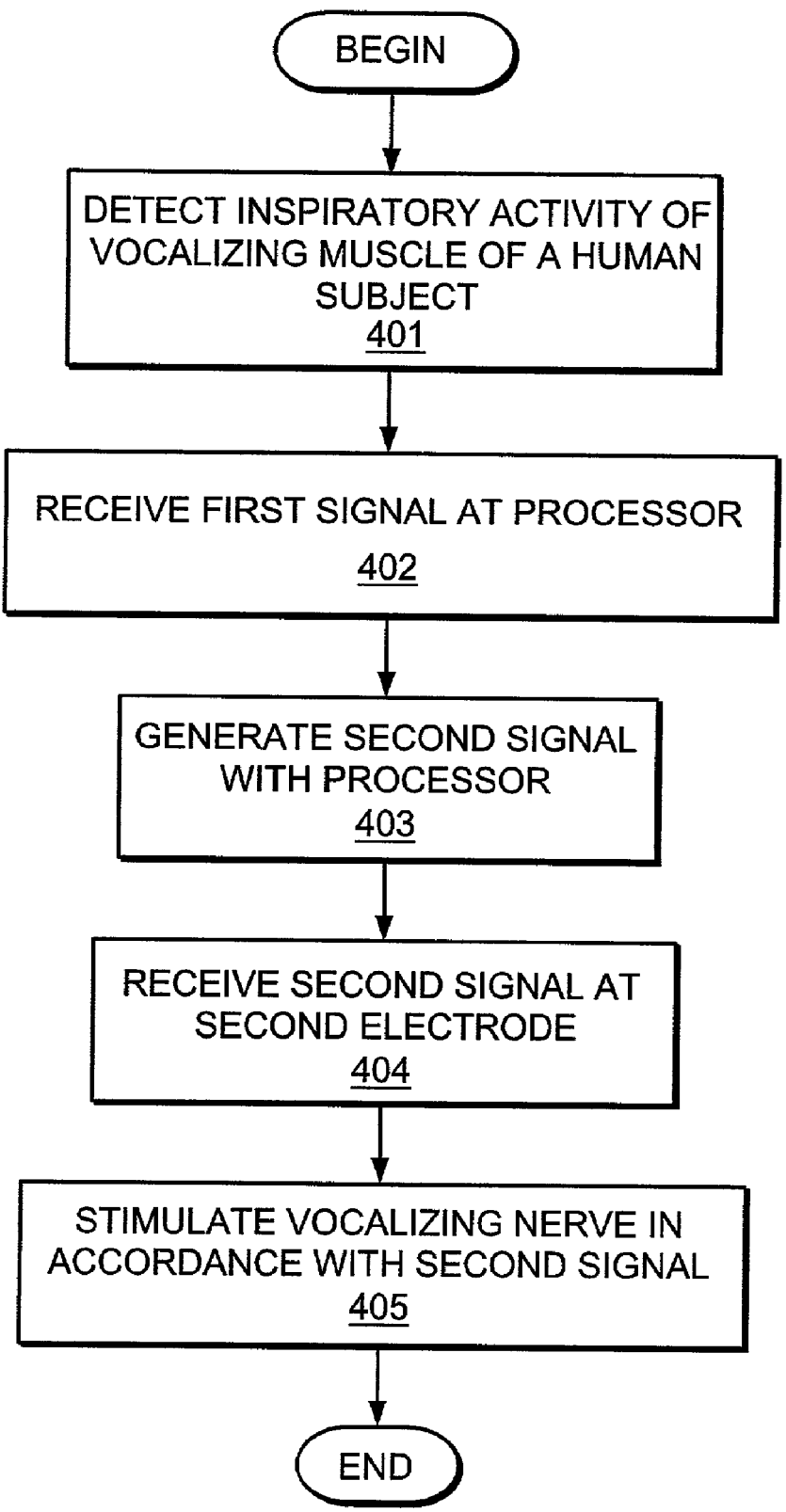
FIG. 4 is a flow chart illustrating a method for stimulating a vocalizing nerve in a human subject having bilateral vocal cord autoparalyis in accordance with another embodiment of the invention.

FIG. 4 is a flow chart illustrating a method for stimulating a vocalizing nerve in a in a human subject having bilateral vocal cord autoparalysis in accordance with another embodiment of the invention. Inspiratory activity of a vocalizing muscle of a human subject, such as infrahyoidal muscles or the diaphram, is detected with a first electrode and a first signal is generated by the first electrode 401. The first signal is received 402 at a processor. Here again, the processor may include a pulse generator. The processor generates 403 a second signal that is substantially synchronous with the first signal. The second signal is received by the second signal at a second electrode 404, and the second electrode stimulates 405 a vocalizing nerve, such as the recurrent laryngeal nerve or the vagus nerve of the subject, in accordance with the second signal.

Figure 5:
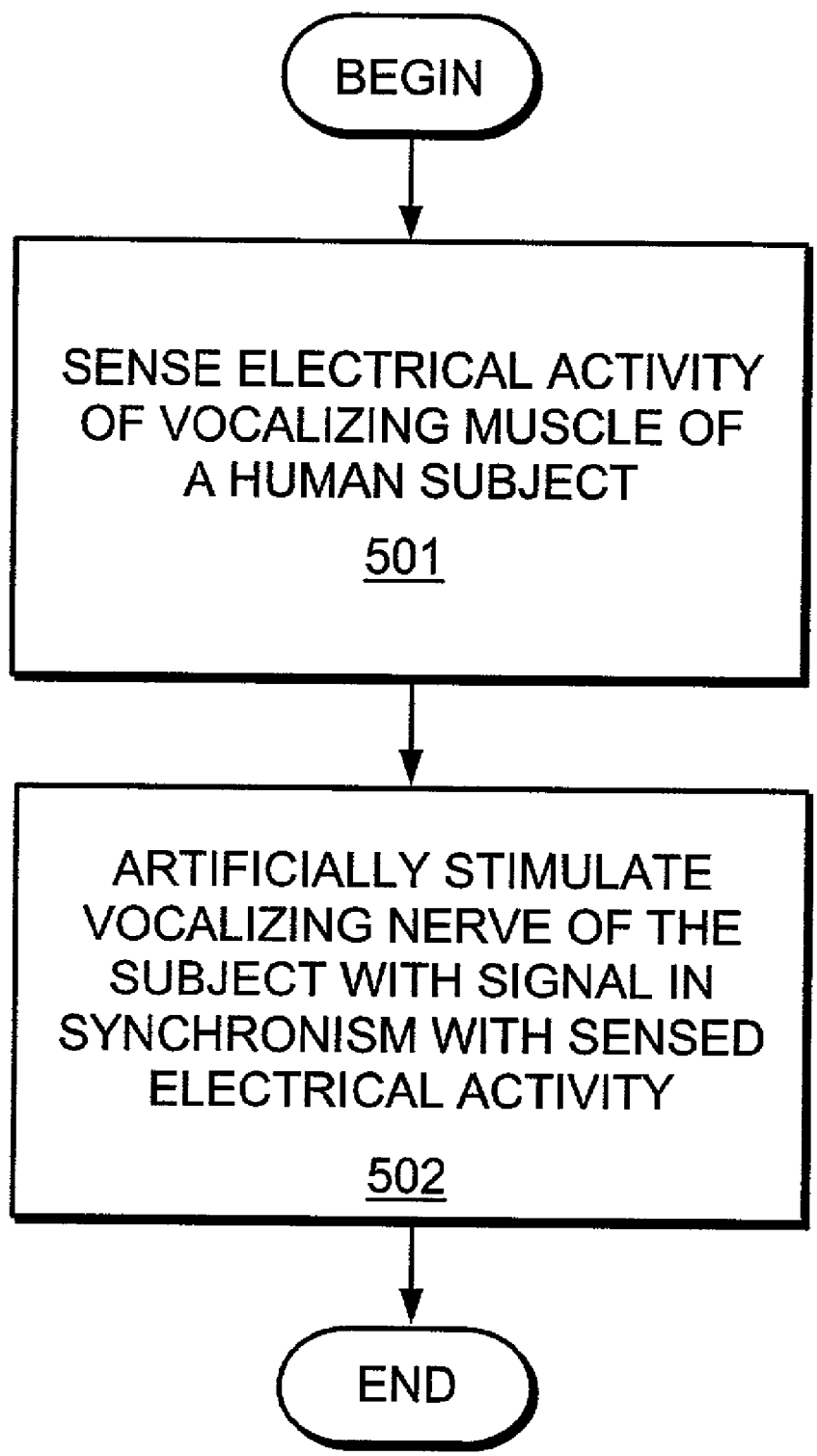
FIG. 5 is a flow chart illustrating a method for pacing laryngeal activity of a human subject in accordance with another embodiment of the invention.

FIG. 5 is a flow chart illustrating a method pacing laryngeal activity of a human subject in accordance with another embodiment of the invention. Electrical activity of a vocalizing muscle (such as the infrahyoidal muscles or the diaphram) of a human subject is sensed 501, and a vocalizing nerve (such as the recurrent laryngeal nerve or the vagus nerve) of the subject is artificially stimulated 502 with an electrical signal in synchronism with the sensed electrical activity. Artificially stimulating the vocalizing nerve of the subject with an electrical signal may include stimulating the nerve with an electrical signal at a frequency that is approximately reciprocal to the contraction time of the vocal cord abductor of the subject. Similarly, artificially stimulating the vocalizing nerve of the subject with an electrical signal may include stimulating the nerve with an electrical signal at a frequency approximately reciprocal to the contraction time of the vocal cord abductor or the subject and below the reciprocal of the contraction time of the vocal cord adductor of the subject.

Figure 6:
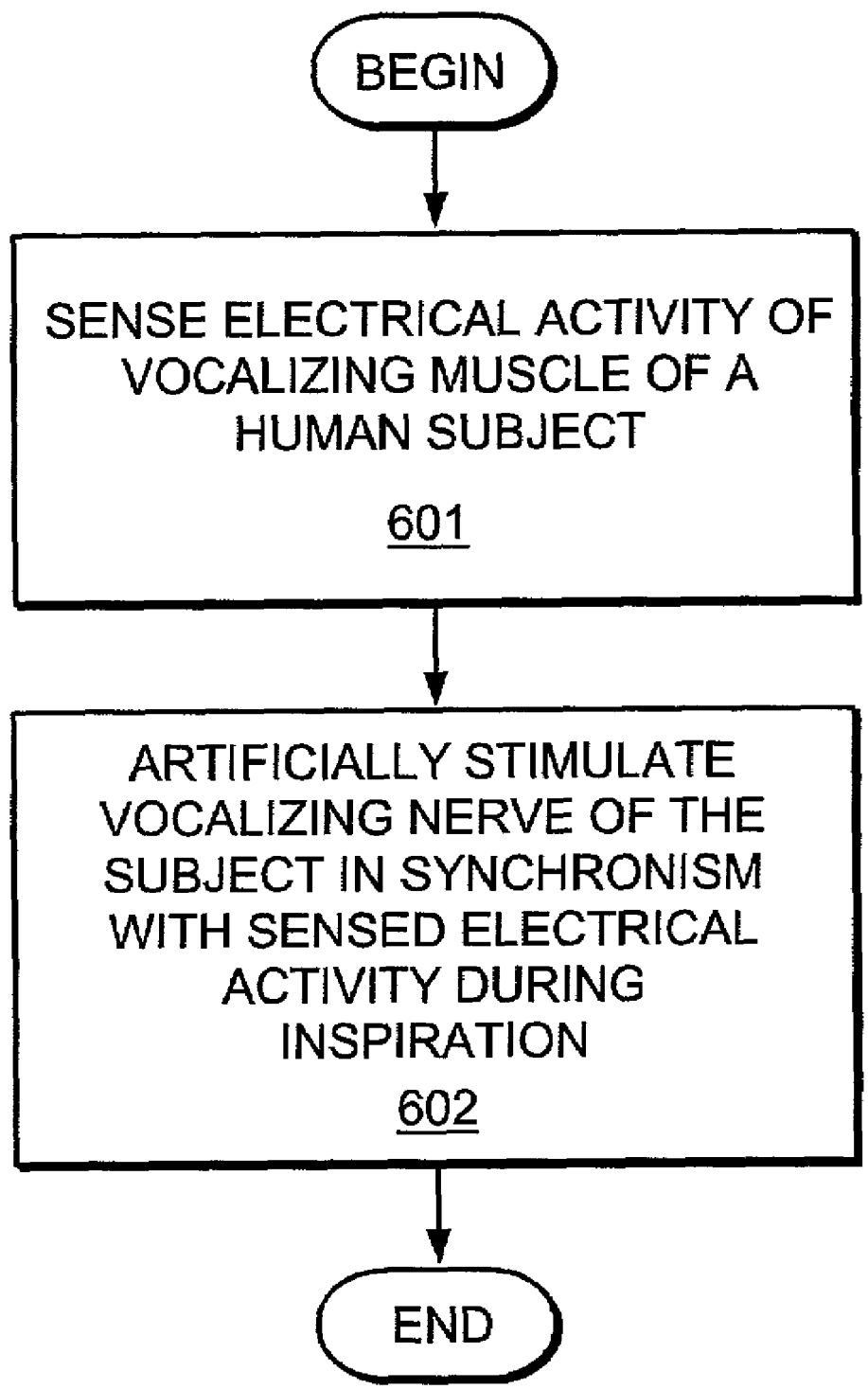
FIG. 6 is a flow chart illustrating a method for pacing laryngeal activity of a human subject accordance with another embodiment of the invention.

FIG. 6 is a flow chart illustrating a method for pacing laryngeal activity of a human subject in accordance with another embodiment of the invention. Electrical activity of a vocalizing muscle of a human subject is sensed 601, and a vocalizing nerve of the subject is artificially stimulated 602 in synchronism with the sensed electrical activity during inspiration such that the subject's vocal folds passively relax backwards to the midline.

While the invention has been described in connection with specific embodiments thereof, it will be understood that it is capable of further modification. This application is intended to cover any variation, uses, or adaptions of the invention and including such departures from the present disclosure as come within known or customary practice in the art to which invention pertains.

What is claimed is:

1. A pacemaker system for a human subject having bilateral vocal cord autoparalysis, the system comprising:
   a sensing electrode for detecting inspiratory activity of a vocalizing muscle of the subject and generating a first signal;
   a processor for receiving the first signal from the sensing electrode and generating a second signal, the second signal being substantially synchronous with the first signal; and
   a stimulating electrode for receiving the second signal from the processor and stimulating a synkinetically reinnervated vocalizing nerve of the subject, the stimulating electrode being adapted to directly contact the vocalizing nerve.

2. A system according to claim 1, wherein the system is partially implantable.

3. A system according to claim 1, wherein the system is totally implantable.

4. A system according to claim 1, further comprising:
   an energy coupling circuit that inductively couples energy for the system through the skin of the subject.

5. A system according to claim 1, further comprising:
   a energy coupling circuit that optically couples energy for the system through the skin of the subject.

6. A system according to claim 1, wherein the vocalizing muscle includes an infrahyoidal muscle of the subject.

7. A system according to claim 1, wherein the vocalizing muscle includes the diaphragm of the subject.

8. A system according to claim 1, wherein the vocalizing nerve includes the recurrent larynegeal nerve of the subject.

9. A system according to claim 1, wherein the vocalizing nerve includes the vagus nerve of the subject.

10. A system according to claim 1, wherein the stimulation electrode is a nerve cuff electrode.

11. A system according to claim 1, wherein the electrodes are bipolar.

12. A system according to claim 1, wherein the electrodes are tripolar.

13. A system according to claim 1, wherein one electrode is bipolar and one electrode is tripolar.

14. A system according to claim 1, wherein the stimulation electrode is fixed to the synkinetically reinnervated vocalizing nerve.

15. A system according to claim 1, wherein the stimulation electrode is inserted into the synkinetically reinnervated vocalizing nerve.

16. A system according to claim 15, wherein the current pulse has a duration of about 0.1 msec to 2 msec and a magnitude in the range of about 0.5 mA to 5.0 mA.

17. A pacemaker for a human subject having bilateral vocal cord autoparalysis, the pacemaker comprising:
    a sensing electrode for detecting inspiratory activity of a vocalizing muscle of the subject and generating a first signal;
    a processor for receiving the first signal from the sensing electrode and generating a second signal, the second signal being substantially synchronous with the first signal; and
    a stimulating electrode for receiving the second signal from the processor and stimulating a synkinetically reinnervated vocalizing nerve of the subject to open the vocal cord and permit inspiration, the stimulating electrode being adapted to directly contact the vocalizing nerve.

18. A pacemaker according to claim 17, wherein the pacemaker is partially implantable.

19. A pacemaker according to claim 17, wherein the pacemaker is totally implantable.

20. A pacemaker according to claim 17, further comprising:
    an energy coupling circuit that inductively couples energy for pacemaker through the skin of the subject.

21. A system according to claim 17, further comprising:
    a energy coupling circuit that optically couples energy for the pacemaker through the skin of the subject.

22. A pacemaker according to claim 17, wherein the vocalizing muscle includes an infrahyoidal muscle of the subject.

23. A pacemaker according to claim 17, wherein the vocalizing muscle includes the diaphragm of the subject.

24. A pacemaker according to claim 17, wherein the vocalizing nerve includes the recurrent larynegeal nerve of the subject.

25. A pacemaker according to claim 17, wherein the vocalizing nerve includes the vagus nerve of the subject.

26. A pacemaker according to claim 17, wherein the processor includes a pulse generator.

27. A pacemaker according to claim 17, wherein the electrodes are bipolar.

28. A pacemaker according to claim 17, wherein the electrodes are tripolar.

29. A pacemaker according to claim 17, wherein one electrode is bipolar and one electrode is tripolar.

30. A pacemaker according to claim 17, wherein the processor detects when the first signal has reached a predetermined level and responds by generating the second signal.

31. A pacemaker according to claim 17, wherein the second signal is a biphase current pulse.

32. A pacemaker according to claim 31, wherein the current pulse has a duration of about 0.1 msec to 2 msec and a magnitude in the range of about 0.5 mA to 5.0 mA.

33. A method for stimulating a vocalizing nerve in a in a human subject having bilateral vocal cord autoparalysis, the method comprising:
  detecting inspiratory activity of a vocalizing muscle of the subject with a first electrode and generating a first signal;
  transmitting the first signal to a processor, the processor generating a second signal, the second signal being substantially synchronous with the first signal; and
  receiving the second signal at a second electrode, the second electrode being in direct contact with a synkinetically reinnervated vocalizing nerve of the subject and stimulating the vocalizing nerve of the subject in accordance with the second signal.

34. A method according to claim 33, further comprising: providing an energy coupling circuit that inductively couples energy through the skin of the subject.

35. A method according to claim 33, further comprising: providing an energy coupling circuit that optically couples energy through the skin of the subject.

36. A method according to claim 33, wherein the vocalizing muscle includes an infrahyoidal muscle of the subject.

37. A method according to claim 33, wherein the vocalizing muscle includes the diaphragm of the subject.

38. A method according to claim 33, wherein the vocalizing nerve includes the recurrent laryngeal nerve of the subject.

39. A method according to claim 33, wherein the vocalizing nerve includes the vagus nerve of the subject.

40. A method according to claim 33, wherein the processor includes a pulse generator.

41. A method according to claim 33, wherein the electrodes are bipolar.

42. A method according to claim 33, wherein the electrodes are tripolar.

43. A method according to claim 33, wherein one electrode is bipolar and one electrode is tripolar.

44. A method according to claim 33, wherein the processor detects when the first signal has reached a predetermined level and responds by generating the second signal.

45. A method according to claim 33, wherein the second signal is a biphase current pulse.

46. A method according to claim 45, wherein the current pulse has a duration of about 0.1 msec to 2 msec and a magnitude in the range of about 0.5 mA to 5.0 mA.

47. A method for pacing laryngeal activity of a human subject, the method comprising:
  sensing electrical activity of a vocalizing muscle of the subject; and
  artificially stimulating a synkinetically reinnervated vocalizing nerve of the subject with an electrode that directly contacts the vocalizing nerve that generates an electrical signal in synchronism with the sensed electrical activity.

48. A method according to claim 47, wherein artificially stimulating the vocalizing nerve of the subject with an electrical signal includes stimulating the nerve with an electrical signal at a frequency that is approximately reciprocal to the contraction time of the vocal cord abductor of the subject.

49. A method according to claim 47, wherein artificially stimulating the vocalizing nerve of the subject with an electrical signal includes stimulating the nerve with an electrical signal at a frequency that is below the reciprocal of the contraction time of the vocal cord adductor of the subject.

50. A method according to claim 47, wherein the vocalizing muscle includes an infrahyoidal muscle of the subject.

51. A method according to claim 47, wherein the vocalizing muscle includes the diaphragm of the subject.

52. A method according to claim 47, wherein the vocalizing nerve includes the recurrent laryngeal nerve of the subject.

53. A method according to claim 47, wherein the vocalizing nerve includes the vagus nerve of the subject.

54. A method for pacing laryngeal activity of a human subject, the method comprising
  sensing electrical activity of a vocalizing muscle of the subject; and
  artificially stimulating a synkinetically reinnervated vocalizing nerve of the subject in synchronism with the sensed electrical activity during inspiration with an electrode that directly contacts the vocalizing nerve such that the subject's vocal folds passively relax backwards to the midline.

55. A method according to claim 54, wherein the vocalizing muscle includes an infrahyoidal muscle of the subject.

56. A method according to claim 54, wherein the vocalizing muscle includes the diaphragm of the subject.

57. A method according to claim 54, wherein the vocalizing nerve includes the recurrent laryngeal nerve of the subject.

58. A method according to claim 54, wherein the vocalizing nerve includes the vagus nerve of the subject.

59. A pacemaker for a human subject having bilateral vocal cord paralysis, the pacemaker comprising:
  an electrode for detecting inspiratory activity of a vocalizing muscle of the subject and generating a first signal;
  a processor for receiving the first signal from the sensing electrode and generating a second signal, the second signal being substantially synchronous with the first signal; and
  an electrode for receiving the second signal from the processor, directly contacting a synkinetically reinnervated vocalizing nerve of the subject and stimulating the vocalizing nerve.

60. A pacemaker for a human subject having bilateral vocal cord autoparalysis, the pacemaker comprising:
  an electrode for detecting inspiratory activity of a vocalizing muscle of the subject and generating a first signal;
  a processor for receiving the first signal from the sensing electrode and generating a second signal; and
  an electrode for receiving the second signal from the processor, directly contacting a synkinetically reinnervated vocalizing nerve of the subject and stimulating the vocalizing nerve.

61. A method for stimulating a vocalizing nerve in a in a human subject having bilateral vocal cord autoparalysis, the method comprising:
  detecting inspiratory activity of a vocalizing muscle of the subject with a sensing electrode and generating a first signal;

transmitting the first signal to a processor, the processor generating a second signal, the second signal being substantially synchronous with the first signal; and receiving the second signal at a stimulating electrode, the stimulating electrode being in direct contact with a synkinetically reinnervated vocalizing nerve of the subject.

62. A method for pacing laryngeal activity of a human subject, the method comprising:

sensing electrical activity of a vocalizing muscle of the subject; and stimulating a vocalizing nerve of the subject with an electrode in direct contact with a synkinetically reinnervated vocalizing nerve that generates an electrical signal in synchronism with the sensed electrical activity.

\* \* \* \* \*

UNITED STATES PATENT AND TRADEMARK OFFICE
CERTIFICATE OF CORRECTION

PATENT NO. : 7,069,082 B2
APPLICATION NO. : 10/117437
DATED : June 27, 2006
INVENTOR(S) : Werner Lindenthaler It is certified that error appears in the above-identified patent and that said Letters Patent is hereby corrected as shown below:

Col. 7, line 16, "in a in a" should be changed to --in a--.

Col. 8, line 23, "comprising" should be changed to --comprising:--.

Col. 8, line 62, "in a in a" should be changed to --in a--.

Signed and Sealed this

Twenty-fourth Day of October, 2006

JON W. DUDAS
*Director of the United States Patent and Trademark Office*